United States Patent [19]
Boyle

[11] Patent Number: 5,843,678
[45] Date of Patent: Dec. 1, 1998

[54] OSTEOPROTEGERIN BINDING PROTEINS

[75] Inventor: William J. Boyle, Moorpark, Calif.

[73] Assignee: Amgen Inc., Thousand Oaks, Calif.

[21] Appl. No.: 842,842

[22] Filed: Apr. 16, 1997

[51] Int. Cl.$^6$ .............................. C12Q 1/00; C07K 14/00
[52] U.S. Cl. .............................. 435/7.1; 514/2; 530/350; 530/300
[58] Field of Search .................................. 530/300, 350; 514/2; 435/7.1

[56] References Cited

U.S. PATENT DOCUMENTS 4,179,337  12/1979  Davis et al. ............................. 435/181

FOREIGN PATENT DOCUMENTS

| | | |
|---|---|---|
| 86/00922 | 2/1986 | WIPO . |
| 90/14363 | 11/1990 | WIPO . |
| WO93/12227 | 6/1993 | WIPO . |
| WO96/26271 | 8/1996 | WIPO . |

OTHER PUBLICATIONS

Chomczynski and Sacchi. Anal. Biochem. 162, 156–159, (1987).
Goeddel, D.V. ed., Methods in Enzymology v. 185, Academic Press (1990).
Gribskov et al. Proc. Natl. Acad. Sci. USA 83, 4355–4359 (1987).
Lüethy et al. Protein Sci. 3, 139–146 (1994).
Montgomery et al. Cell 87, 427–436 (1996).
Nagata and Golstein, Science 267, 1449–1456 (1995).
Pearson, Meth. Enzymol. 183, 63–98 (1990).
*Remington's Pharmaceutical Sciences*, 18th ed. A.R. Gennaro, ed. Mack, Easton, PA (1980).
Sambrook et al. *Molecular Cloning: A Laboratory Manual* Cold Spring Harbor Press, New York (1989).
Wiley et al. Immunity 3, 673–682 (1995).
Simonet et al. Apr. 18, 1997 Cell 89:309–319.

*Primary Examiner*—Karen Carlson
*Attorney, Agent, or Firm*—Robert B. Winter; Steven M. Odre; Ron K. Levy

[57] ABSTRACT

A novel polypeptide, osteoprotegerin binding protein, involved in osteolcast maturation has been identified based upon its affinity for osteoprotegerin. Nucleic acid sequences encoding the polypeptide, or a fragment, analog or derivative thereof, vectors and host cells for production, methods of preparing osteoprotegerin binding protein, and binding assays are also described. Compositions and methods for the treatment of bone diseases such as osteoporosis, bone loss due to arthritis or metastasis, hypercalcemia, and Paget's disease are also provided.

15 Claims, 10 Drawing Sheets

FIG.1A

```
GAGCTCGGAT CCACTACTCG ACCCACGCGT CCGGCCAGGA CCTCTGTGAA CCGGTCGGGG     60

CGGGGCCGC CTGGCCCGGGA GTCTGCTCGG CGGTGGGTGG CCGAGGAAGG GAGAGAACGA    120

TCGCGGAGCA GGGCGCCCGA ACTCCGGGGCG CCGCGCC ATG CGC CGG GCC AGC CGA    175
                                          Met Arg Arg Ala Ser Arg
                                           1               5

GAC TAC GGC AAG TAC CTG CGC AGC TCG GAG GAG ATG GGC AGC GGC CCC      223
Asp Tyr Gly Lys Tyr Leu Arg Ser Ser Glu Glu Met Gly Ser Gly Pro
        10                      15                      20

GGC GTC CCA CAC GAG GGT CCG CTG CAC CCC GCG CCT TCT GCA CCG GCT      271
Gly Val Pro His Glu Gly Pro Leu His Pro Ala Pro Ser Ala Pro Ala
        25                      30                      35
```

FIG. 1B

```
CCG GCG CCG CCA CCC GCC GCC TCC CGC TCC ATG TTC CTC CTG GCC CTC CTG    319
Pro Ala Pro Pro Pro Ala Ala Ser Arg Ser Met Phe Leu Ala Leu Leu
     40                  45                  50

GGG CTG GGA CTG GGC CAG GTG TGC AGC ATC GCT CTG TTC CTG TAC            367
Gly Leu Gly Leu Gly Gln Val Cys Ser Ile Ala Leu Phe Leu Tyr
 55                  60                  65                  70

TTT CGA GCG CAG ATG GAT CCT AAC AGA ATA TCA GAA GAC AGC ACT CAC        415
Phe Arg Ala Gln Met Asp Pro Asn Arg Ile Ser Glu Asp Ser Thr His
             75                  80                  85

TGC TTT TAT AGA ATC CTG AGA CTC CAT GAA AAC GCA GGT TTG CAG GAC        463
Cys Phe Tyr Arg Ile Leu Arg Leu His Glu Asn Ala Gly Leu Gln Asp
         90                  95                 100

TCG ACT CTG GAG AGT GAA GAC ACA CTA CCT GAC TCC TGC AGG AGG ATG        511
Ser Thr Leu Glu Ser Glu Asp Thr Leu Pro Asp Ser Cys Arg Arg Met
     105                 110                 115
```

FIG.1C

```
AAA CAA GCC TTT CAG GGG GCC GTG CAG AAG GAA CTG CAA CAC ATT GTG     559
Lys Gln Ala Phe Gln Gly Ala Val Gln Lys Glu Leu Gln His Ile Val
        120                 125                 130

GGG CCA CAG CGC TTC TCA GGA GCT CCA GCT ATG ATG GAA GGC TCA TGG     607
Gly Pro Gln Arg Phe Ser Gly Ala Pro Ala Met Met Glu Gly Ser Trp
        135                 140                 145                 150

TTG GAT GTG GCC CAG CGA GGC AAG CCT GAG GCC CAG CCA TTT GCA CAC     655
Leu Asp Val Ala Gln Arg Gly Lys Pro Glu Ala Gln Pro Phe Ala His
        155                 160                 165

CTC ACC ATC AAT GCT GCC AGC ATC CCA TCG GGT TCC CAT AAA GTC ACT     703
Leu Thr Ile Asn Ala Ala Ser Ile Pro Ser Gly Ser His Lys Val Thr
        170                 175                 180
```

FIG.1D

```
CTG TCC TCT TGG TAC CAC GAT CGA GGC TGG GCC AAG ATC TCT AAC ATG    751
Leu Ser Ser Trp Tyr His Asp Arg Gly Trp Ala Lys Ile Ser Asn Met
        185                     190                     195

ACG TTA AGC AAC GGA AAA CTA AGG GTT AAC CAA GAT GGC TTC TAT TAC    799
Thr Leu Ser Asn Gly Lys Leu Arg Val Asn Gln Asp Gly Phe Tyr Tyr
        200                     205                     210

CTG TAC GCC AAC ATT TGC TTT CGG CAT CAT GAA ACA TCG GGA AGC GTA    847
Leu Tyr Ala Asn Ile Cys Phe Arg His His Glu Thr Ser Gly Ser Val
        215                     220                     225                230

CCT ACA GAC TAT CTT CAG CTG ATG GTG TAT GTC GTT AAA ACC AGC ATC    895
Pro Thr Asp Tyr Leu Gln Leu Met Val Tyr Val Val Lys Thr Ser Ile
        235                     240                     245
```

FIG.1E

```
AAA ATC CCA AGT TCT CAT AAC CTG ATG AAA GGA GGG AGC ACG AAA AAC     943
Lys Ile Pro Ser Ser His Asn Leu Met Lys Gly Gly Ser Thr Lys Asn
        250                 255                 260

TGG TCG GGC AAT TCT GAA TTC CAC TTT TAT TCC ATA AAT GTT GGG GGA     991
Trp Ser Gly Asn Ser Glu Phe His Phe Tyr Ser Ile Asn Val Gly Gly
        265                 270                 275

TTT TTC AAG CTC CGA GCT GGT GAA GAA ATT AGC ATT CAG GTG TCC AAC    1039
Phe Phe Lys Leu Arg Ala Gly Glu Glu Ile Ser Ile Gln Val Ser Asn
        280                 285                 290

CCT TCC CTG CTG GAT CAA GAT CCG GAT GCG ACG TAC TTT GGG GCT TTC    1087
Pro Ser Leu Leu Asp Gln Asp Pro Asp Ala Thr Tyr Phe Gly Ala Phe
        295                 300                 305         310

AAA GTT CAG GAC ATA GAC T GAGACTCATT TCGTGGAACA TTAGCATGGA         1136
Lys Val Gln Asp Ile Asp
        315
```

FIG.1F

| | | | | | |
|---|---|---|---|---|---|
| TGTCCTAGAT | GTTGGAAAAC | TTCTTAAAAA | ATGGATGATG | TCTATACATG | TGTAAGACTA | 1196
| CTAAGAGACA | TGGCCCACGG | TGTATGAAAC | TCACAGCCCT | CTCTCTTGAG | CCTGTACAGG | 1256
| TTGTGTATAT | GTAAAGTCCA | TAGGTGATGT | TAGATTCATG | GTGATTACAC | AACGGTTTTA | 1316
| CAATTTTGTA | ATGATTTCCT | AGAATTGAAC | CAGATTGGGA | GAGGTATTCC | GATGCTTATG | 1376
| AAAAACTTAC | ACGTGAGCTA | TGGAAGGGGG | TCACAGTCTC | TGGGTCTAAC | CCCTGGACAT | 1436
| GTGCCACTGA | GAACCTTGAA | ATTAAGAGGA | TGCCATGTCA | TTGCAAAGAA | ATGATAGTGT | 1496
| GAAGGGTTAA | GTTCTTTTGA | ATTGTTACAT | TGCGCTGGGA | CCTGCAAATA | AGTTCTTTTT | 1556

FIG.1G

```
TTCTAATGAG GAGAGAAAAA TATATGTATT TTTATATAAT GTCTAAAGTT ATATTTCAGG   1616
TGTAATGTTT TCTGTGCAAA GTTTGTAAA  TTATATTTGT GCTATAGTAT TTGATTCAAA   1676
ATATTTAAAA ATGTCTCACT GTTGACATAT TTAATGTTTT AAATGTACAG ATGTATTTAA   1736
CTGGTGCACT TTGTAATTCC CCTGAAGGTA CTCGTAGCTA AGGGGGCAGA ATACTGTTTC   1796
TGGTGACCAC ATGTAGTTTA TTTCTTTATT CTTTTTAACT TAATAGAGTC TTCAGACTTG   1856
TCAAAACTAT GCAAGCAAAA TAAATAAATA AAAATAAAAT GAATACCCTG AATAATAAGT   1916
AGGATGTTGG TCACCAGGTG CCTTTCAAAT TTAGAAGCTA ATTGACTTTA GGAGCTGACA   1976
TAGCCAAAAA GGATACATAA TAGGCTACTG AAATCTGTCA GGAGTATTTA TGCAATTATT   2036
```

FIG.1H

```
GAACAGGTGT CTTTTTTAC AAGAGCTACA AATTGTAAAT TTTGTTTCTT TTTTTTCCCA    2096
TAGAAAATGT ACTATAGTTT ATCAGCCAAA AAACAATCCA CTTTTTAATT TAGTGAAAGT    2156
TATTTTATTA TACTGTACAA TAAAAGCATT GTCTCTGAAT GTTAATTTTT TGGTACAAAA    2216
AATAAATTTG TACGAAAACC TGAAAAAAAA AAAAAAAAAA AAAAAAAGGG CGGCCGCTCT    2276
AGAGGGCCCT ATTCTATAG                                                 2295
```

ID

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GTTCTCCTCA TATGGATCCA AACCGTATTT CTGAAGACAG CACTCACTGC TT    52

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA -continued ( x i ) SEQUENCE DESCRIPTION: SEQ ID NO:2:

TACGCACTCC GCGGTTAGTC TATGTCCTGA ACTTTGA                                    37

( 2 ) INFORMATION FOR SEQ ID NO:3:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GTTCTCCTCA TATGAAACCT GAAGCTCAAC CATTTGCACA CCTCACCATC AAT                  53

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GTTCTCCTCA TATGCATTTA ACTATTAACG CTGCATCTAT CCCAT                           45

( 2 ) INFORMATION FOR SEQ ID NO:5:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GTTCTCCTCA TATGACTATT AACGCTGCAT CTATCCCATC GGGTTCCCAT AAAGTCACT            59

( 2 ) INFORMATION FOR SEQ ID NO:6:

( i ) SEQUENCE CHARACTERISTICS:
        ( A ) LENGTH: 2295 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 158..1105

( x i ) SEQUENCE DESCRIPTION: SEQ ID NO:6:

GAGCTCGGAT CCACTACTCG ACCCACGCGT CCGGCCAGGA CCTCTGTGAA CCGGTCGGGG           60

CGGGGGCCGC CTGGCCGGGA GTCTGCTCGG CGGTGGGTGG CCGAGGAAGG GAGAGAACGA          120

TCGCGGAGCA GGGCGCCCGA ACTCCGGGCG CCGCGCC ATG CGC CGG GCC AGC CGA          175
                                                            Met Arg Arg Ala Ser Arg
                                                             1                       5

GAC TAC GGC AAG TAC CTG CGC AGC TCG GAG GAG ATG GGC AGC GGC CCC           223
Asp Tyr Gly Lys Tyr Leu Arg Ser Ser Glu Glu Met Gly Ser Gly Pro
             10                        15                       20

GGC GTC CCA CAC GAG GGT CCG CTG CAC CCC GCG CCT TCT GCA CCG GCT           271

```
              Gly  Val  Pro  His  Glu  Gly  Pro  Leu  His  Pro  Ala  Pro  Ser  Ala  Pro  Ala
                         25                  30                  35

CCG  GCG  CCG  CCA  CCC  GCC  GCC  TCC  CGC  TCC  ATG  TTC  CTG  GCC  CTC  CTG      319
              Pro  Ala  Pro  Pro  Pro  Ala  Ala  Ser  Arg  Ser  Met  Phe  Leu  Ala  Leu  Leu
                         40                  45                  50

GGG  CTG  GGA  CTG  GGC  CAG  GTG  GTC  TGC  AGC  ATC  GCT  CTG  TTC  CTG  TAC      367
              Gly  Leu  Gly  Leu  Gly  Gln  Val  Val  Cys  Ser  Ile  Ala  Leu  Phe  Leu  Tyr
               55                  60                  65                  70

TTT  CGA  GCG  CAG  ATG  GAT  CCT  AAC  AGA  ATA  TCA  GAA  GAC  AGC  ACT  CAC      415
              Phe  Arg  Ala  Gln  Met  Asp  Pro  Asn  Arg  Ile  Ser  Glu  Asp  Ser  Thr  His
                              75                  80                  85

TGC  TTT  TAT  AGA  ATC  CTG  AGA  CTC  CAT  GAA  AAC  GCA  GGT  TTG  CAG  GAC      463
              Cys  Phe  Tyr  Arg  Ile  Leu  Arg  Leu  His  Glu  Asn  Ala  Gly  Leu  Gln  Asp
                         90                  95                 100

TCG  ACT  CTG  GAG  AGT  GAA  GAC  ACA  CTA  CCT  GAC  TCC  TGC  AGG  AGG  ATG      511
              Ser  Thr  Leu  Glu  Ser  Glu  Asp  Thr  Leu  Pro  Asp  Ser  Cys  Arg  Arg  Met
                        105                 110                 115

AAA  CAA  GCC  TTT  CAG  GGG  GCC  GTG  CAG  AAG  GAA  CTG  CAA  CAC  ATT  GTG      559
              Lys  Gln  Ala  Phe  Gln  Gly  Ala  Val  Gln  Lys  Glu  Leu  Gln  His  Ile  Val
                        120                 125                 130

GGG  CCA  CAG  CGC  TTC  TCA  GGA  GCT  CCA  GCT  ATG  ATG  GAA  GGC  TCA  TGG      607
              Gly  Pro  Gln  Arg  Phe  Ser  Gly  Ala  Pro  Ala  Met  Met  Glu  Gly  Ser  Trp
              135                 140                 145                 150

TTG  GAT  GTG  GCC  CAG  CGA  GGC  AAG  CCT  GAG  GCC  CAG  CCA  TTT  GCA  CAC      655
              Leu  Asp  Val  Ala  Gln  Arg  Gly  Lys  Pro  Glu  Ala  Gln  Pro  Phe  Ala  His
                                  155                 160                 165

CTC  ACC  ATC  AAT  GCT  GCC  AGC  ATC  CCA  TCG  GGT  TCC  CAT  AAA  GTC  ACT      703
              Leu  Thr  Ile  Asn  Ala  Ala  Ser  Ile  Pro  Ser  Gly  Ser  His  Lys  Val  Thr
                             170                 175                 180

CTG  TCC  TCT  TGG  TAC  CAC  GAT  CGA  GGC  TGG  GCC  AAG  ATC  TCT  AAC  ATG      751
              Leu  Ser  Ser  Trp  Tyr  His  Asp  Arg  Gly  Trp  Ala  Lys  Ile  Ser  Asn  Met
                        185                 190                 195

ACG  TTA  AGC  AAC  GGA  AAA  CTA  AGG  GTT  AAC  CAA  GAT  GGC  TTC  TAT  TAC      799
              Thr  Leu  Ser  Asn  Gly  Lys  Leu  Arg  Val  Asn  Gln  Asp  Gly  Phe  Tyr  Tyr
                        200                 205                 210

CTG  TAC  GCC  AAC  ATT  TGC  TTT  CGG  CAT  CAT  GAA  ACA  TCG  GGA  AGC  GTA      847
              Leu  Tyr  Ala  Asn  Ile  Cys  Phe  Arg  His  His  Glu  Thr  Ser  Gly  Ser  Val
              215                 220                 225                 230

CCT  ACA  GAC  TAT  CTT  CAG  CTG  ATG  GTG  TAT  GTC  GTT  AAA  ACC  AGC  ATC      895
              Pro  Thr  Asp  Tyr  Leu  Gln  Leu  Met  Val  Tyr  Val  Val  Lys  Thr  Ser  Ile
                                  235                 240                 245

AAA  ATC  CCA  AGT  TCT  CAT  AAC  CTG  ATG  AAA  GGA  GGG  AGC  ACG  AAA  AAC      943
              Lys  Ile  Pro  Ser  Ser  His  Asn  Leu  Met  Lys  Gly  Gly  Ser  Thr  Lys  Asn
                             250                 255                 260

TGG  TCG  GGC  AAT  TCT  GAA  TTC  CAC  TTT  TAT  TCC  ATA  AAT  GTT  GGG  GGA      991
              Trp  Ser  Gly  Asn  Ser  Glu  Phe  His  Phe  Tyr  Ser  Ile  Asn  Val  Gly  Gly
                        265                 270                 275

TTT  TTC  AAG  CTC  CGA  GCT  GGT  GAA  GAA  ATT  AGC  ATT  CAG  GTG  TCC  AAC     1039
              Phe  Phe  Lys  Leu  Arg  Ala  Gly  Glu  Glu  Ile  Ser  Ile  Gln  Val  Ser  Asn
                        280                 285                 290

CCT  TCC  CTG  CTG  GAT  CCG  GAT  CAA  GAT  GCG  ACG  TAC  TTT  GGG  GCT  TTC     1087
              Pro  Ser  Leu  Leu  Asp  Pro  Asp  Gln  Asp  Ala  Thr  Tyr  Phe  Gly  Ala  Phe
              295                 300                 305                 310

AAA  GTT  CAG  GAC  ATA  GAC  TGAGACTCAT  TTCGTGGAAC  ATTAGCATGG                  1135
              Lys  Val  Gln  Asp  Ile  Asp
                                  315

ATGTCCTAGA  TGTTTGGAAA  CTTCTTAAAA  AATGGATGAT  GTCTATACAT  GTGTAAGACT            1195

ACTAAGAGAC  ATGGCCCACG  GTGTATGAAA  CTCACAGCCC  TCTCTCTTGA  GCCTGTACAG            1255

GTTGTGTATA  TGTAAAGTCC  ATAGGTGATG  TTAGATTCAT  GGTGATTACA  CAACGGTTTT            1315
```

| | | | | | |
|---|---|---|---|---|---|
| ACAATTTTGT | AATGATTTCC | TAGAATTGAA | CCAGATTGGG | AGAGGTATTC | CGATGCTTAT | 1375 |
| GAAAAACTTA | CACGTGAGCT | ATGGAAGGGG | GTCACAGTCT | CTGGGTCTAA | CCCCTGGACA | 1435 |
| TGTGCCACTG | AGAACCTTGA | AATTAAGAGG | ATGCCATGTC | ATTGCAAAGA | AATGATAGTG | 1495 |
| TGAAGGGTTA | AGTTCTTTTG | AATTGTTACA | TTGCGCTGGG | ACCTGCAAAT | AAGTTCTTTT | 1555 |
| TTTCTAATGA | GGAGAGAAAA | ATATATGTAT | TTTTATATAA | TGTCTAAAGT | TATATTTCAG | 1615 |
| GTGTAATGTT | TTCTGTGCAA | AGTTTTGTAA | ATTATATTTG | TGCTATAGTA | TTTGATTCAA | 1675 |
| AATATTTAAA | AATGTCTCAC | TGTTGACATA | TTTAATGTTT | TAAATGTACA | GATGTATTTA | 1735 |
| ACTGGTGCAC | TTTGTAATTC | CCCTGAAGGT | ACTCGTAGCT | AAGGGGGCAG | AATACTGTTT | 1795 |
| CTGGTGACCA | CATGTAGTTT | ATTTCTTTAT | TCTTTTTAAC | TTAATAGAGT | CTTCAGACTT | 1855 |
| GTCAAAACTA | TGCAAGCAAA | ATAAATAAAT | AAAAATAAAA | TGAATACCTT | GAATAATAAG | 1915 |
| TAGGATGTTG | GTCACCAGGT | GCCTTTCAAA | TTTAGAAGCT | AATTGACTTT | AGGAGCTGAC | 1975 |
| ATAGCCAAAA | AGGATACATA | ATAGGCTACT | GAAATCTGTC | AGGAGTATTT | ATGCAATTAT | 2035 |
| TGAACAGGTG | TCTTTTTTTA | CAAGAGCTAC | AAATTGTAAA | TTTTGTTTCT | TTTTTTTCCC | 2095 |
| ATAGAAAATG | TACTATAGTT | TATCAGCCAA | AAAACAATCC | ACTTTTTAAT | TTAGTGAAAG | 2155 |
| TTATTTTATT | ATACTGTACA | ATAAAAGCAT | TGTCTCTGAA | TGTTAATTTT | TTGGTACAAA | 2215 |
| AAATAAATTT | GTACGAAAAC | CTGAAAAAAA | AAAAAAAAA | AAAAAAAGG | GCGGCCGCTC | 2275 |
| TAGAGGGCCC | TATTCTATAG | | | | | 2295 |

( 2 ) INFORMATION FOR SEQ ID NO:7:

( i ) SEQUENCE CHARACTERISTICS:
        ( A ) LENGTH: 316 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Arg Arg Ala Ser Arg Asp Tyr Gly Lys Tyr Leu Arg Ser Ser Glu
 1               5                  10                  15

Glu Met Gly Ser Gly Pro Gly Val Pro His Glu Gly Pro Leu His Pro
                20                  25                  30

Ala Pro Ser Ala Pro Ala Pro Ala Pro Pro Ala Ala Ser Arg Ser
            35                  40                  45

Met Phe Leu Ala Leu Leu Gly Leu Gly Leu Gly Gln Val Val Cys Ser
        50                  55                  60

Ile Ala Leu Phe Leu Tyr Phe Arg Ala Gln Met Asp Pro Asn Arg Ile
65                  70                  75                  80

Ser Glu Asp Ser Thr His Cys Phe Tyr Arg Ile Leu Arg Leu His Glu
                85                  90                  95

Asn Ala Gly Leu Gln Asp Ser Thr Leu Glu Ser Glu Asp Thr Leu Pro
               100                 105                 110

Asp Ser Cys Arg Arg Met Lys Gln Ala Phe Gln Gly Ala Val Gln Lys
           115                 120                 125

Glu Leu Gln His Ile Val Gly Pro Gln Arg Phe Ser Gly Ala Pro Ala
       130                 135                 140

Met Met Glu Gly Ser Trp Leu Asp Val Ala Gln Arg Gly Lys Pro Glu
145                 150                 155                 160

Ala Gln Pro Phe Ala His Leu Thr Ile Asn Ala Ala Ser Ile Pro Ser
                165                 170                 175
```

| | | | | | | | | | | | | | |
|---|---|---|---|---|---|---|---|---|---|---|---|---|---|
|Gly|Ser|His|Lys 180|Val|Thr|Leu|Ser|Ser 185|Trp|Tyr|His|Asp|Arg 190|Gly|Trp|
|Ala|Lys|Ile 195|Ser|Asn|Met|Thr|Leu 200|Ser|Asn|Gly|Lys|Leu 205|Arg|Val|Asn|
|Gln|Asp 210|Gly|Phe|Tyr|Tyr|Leu 215|Tyr|Ala|Asn|Ile|Cys 220|Phe|Arg|His|His|
|Glu 225|Thr|Ser|Gly|Ser|Val 230|Pro|Thr|Asp|Tyr|Leu 235|Gln|Leu|Met|Val|Tyr 240|
|Val|Val|Lys|Thr|Ser 245|Ile|Lys|Ile|Pro|Ser 250|Ser|His|Asn|Leu|Met 255|Lys|
|Gly|Gly|Ser|Thr 260|Lys|Asn|Trp|Ser|Gly 265|Asn|Ser|Glu|Phe|His 270|Phe|Tyr|
|Ser|Ile|Asn 275|Val|Gly|Gly|Phe|Phe 280|Lys|Leu|Arg|Ala|Gly 285|Glu|Glu|Ile|
|Ser|Ile 290|Gln|Val|Ser|Asn|Pro 295|Ser|Leu|Leu|Asp|Pro 300|Asp|Gln|Asp|Ala|
|Thr 305|Tyr|Phe|Gly|Ala|Phe 310|Lys|Val|Gln|Asp|Ile 315|Asp|

OSTEOPROTEGERIN BINDING PROTEINS

FIELD OF THE INVENTION

The present invention relates to polypeptides which are involved in osteoclast differentiation. More particularly, the invention relates to osteoprotegerin binding proteins, nucleic acids encoding the proteins, expression vectors and host cells for production of the proteins, and binding assays. Compositions and methods for the treatment of bone diseases, such as osteoporosis, bone loss from arthritis, Paget's disease, and hypercalcemia, are also described.

BACKGROUND OF THE INVENTION

Living bone tissue exhibits a dynamic equilibrium between deposition and resorption of bone. These processes are mediated primarily by two cell types: osteoblasts, which secrete molecules that comprise the organic matrix of bone; and osteoclasts, which promote dissolution of the bone matrix and solubilization of bone salts. In young individuals with growing bone, the rate of bone deposition exceeds the rate of bone resorption, while in older individuals the rate of resorption can exceed deposition. In the latter situation, the increased breakdown of bone leads to reduced bone mass and strength, increased risk of fractures, and slow or incomplete repair of broken bones.

Osteoclasts are large phagocytic multinucleated cells which are formed from hematopoietic precursor cells in the bone marrow. Although the growth and formation of mature functional osteoclasts is not well understood, it is thought that osteoclasts mature along the monocyte/macrophage cell lineage in response to exposure to various growth-promoting factors. Early development of bone marrow precursor cells to preosteoclasts are believed to mediated by soluble factors such as tumor necrosis factor-α (TNF-α), tumor necrosis factor-β (TNF-β), interleukin-1 (IL-1), interleukin-4 (IL-4), interleukin-6 (IL-6), and leukemia inhibitory factor (LIF). In culture, preosteoclasts are formed in the presence of added macrophage colony stimualting factor (M-CSF). These factors act primarily in early steps of osteoclast development. The involvement of polypeptide factors in terminal stages of osteoclast formation has not been extensively reported. It has been reported, however, that parathyroid hormone stimulates the formation and activity of osteoclasts and that calcitonin has the opposite effect, although to a lesser extent.

Recently, a new polypeptide factor, termed osteoprotegerin (OPG), has been described which negatively regulated formation of osteoclasts in vitro and in vivo (see co-owned and co-pending U.S. Ser. Nos. 08/577,788 filed Dec. 22, 1995, 08/706,945 filed Sep. 3, 1996, and 08/771,777, filed Dec. 20, 1996, hereby incorporated by reference; and PCT Application No. WO96/26271). OPG dramatically increased the bone density in transgenic mice expressing the OPG polypeptide and reduced the extent of bone loss when administered to ovariectomized rats. An analysis of OPG activity in in vitro osteoclast formation revealed that OPG does not interfere with the growth and differentiation of monocyte/macrophage precursors, but more likely blocks the differentiation of ostoeclasts from monocyte/macrophage precursors. Thus OPG appears to have specificity in regulating the extent of osteoclast formation.

OPG comprises two polypeptide domains having different structural and functional properties. The amino-terminal domain spanning about residues 22-194 of the full-length polypeptide (the N-terminal methionine is designated residue 1) shows homology to other members of the tumor necrosis factor receptor (TNFR) family, especially TNFR-2, through conservation of cysteine rich domains characteristic of TNFR family members. The carboxy terminal domain spanning residues 194-401 has no significant homology to any known sequences. Unlike a number of other TNFR family members, OPG appears to be exclusively a secreted protein and does not appear to be synthesized as a membrane associated form.

Based upon its activity as a negative regulator of osteoclast formation, it is postulated that OPG may bind to a polypeptide factor involved in osteoclast differentiation and thereby block one or more terminal steps leading to formation of a mature osteoclast.

It is therefore an object of the invention to identify polypeptides which interact with OPG. Said polypeptides may play a role in osteoclast maturation and may be useful in the treatment of bone diseases.

SUMMARY OF THE INVENTION

A novel member of the tumor necrosis factor family has been identified from a murine cDNA library expressed in COS cells screened using a recombinant OPG-Fc fusion protein as an affinity probe. The new polypeptide is a transmembrane OPG binding protein which is predicted to be 316 amino acids in length, and has an amino terminal cytoplasmic domain, a transmembrane doman, and a carboxy terminal extracellular domain. OPG binding proteins of the invention may be membrane-associated or may be in soluble form.

The invention provides for nucleic acids encoding an OPG binding protein, vectors and host cells expressing the polypeptide, and method for producing recombinant OPG binding protein. Antibodies or fragments thereof which specifically bind OPG binding protein are also provided.

OPG binding proteins may be used in assays to quantitate OPG levels in biological samples, identify cells and tissues that display OPG binding protein, and identify new OPG and OPG binding protein family members. Methods of identifying compounds which interact with OPG binding protein are also provided. Such compounds include nucleic acids, peptides, proteins, carbohydrates, lipids or small molecular weight organic molecules and may act either as agonists or antagonists of OPG binding protein activity.

OPG binding proteins are involved in osteoclast differentiation and the level of osteoclast activity in turn modulates bone resorption. OPG binding protein agonists and antagonists modulate osteoclast formation and bone resorption and may be used to treat bone diseases characterized by changes in bone resorption, such as osteoporosis, hypercalcemia, bone loss due to arthritis or metastasis, Paget's disease, osteopetrosis and the like. Pharmaceutical compositions comprising OPG binding proteins and OPG binding protein agonists and antagonists are also encompassed by the invention.

DESCRIPTION OF THE FIGURES

FIG. 1. Structure and sequence of the 32D-F3 insert encoding OPG binding protein. Predicted transmembrane domain and sites for asparagine-linked carbohydrate chains are underlined.

DETAILED DESCRIPTION OF THE INVENTION

Figure 2:
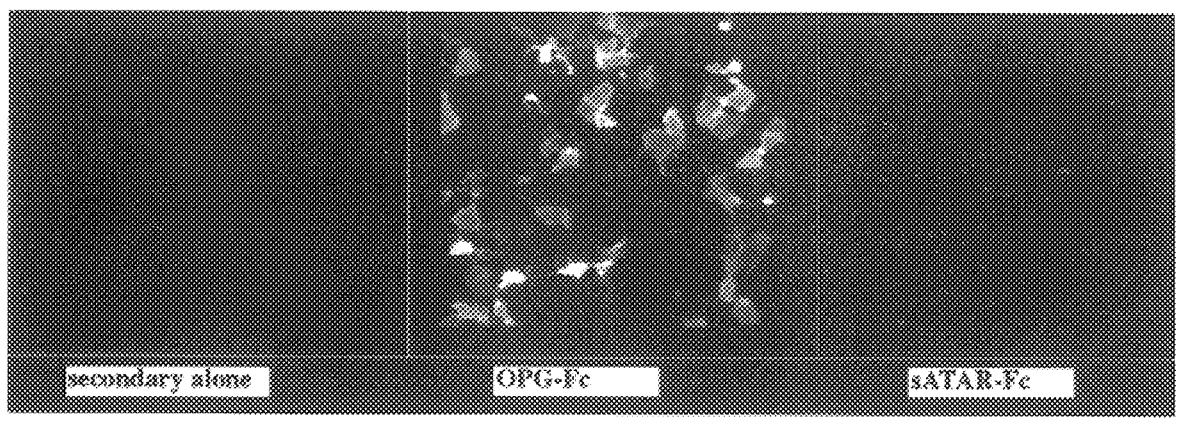
FIG. 2. OPG binding protein expression in COS-7 cells transfected with pcDNA/32D-F3. Cells were lipofected with pcDNA/32D-F3 DNA, then assayed for binding to either goat anti-human IgG1 alkaline phosphatase conjugate (secondary alone), human OPG[22-201]-Fc plus secondary (OPG-Fc), or a chimeric ATAR extracellular domain-Fc fusion protein (sATAR-Fc). ATAR is a new member of the TNFR superfamily, and the sATAR-Fc fusion protein serves as a control for both human IgG1 Fc domain binding, and generic TNFR releated protein, binding to 32D cell surface molecules.

The invention provides for a polypeptide referred to as an OPG binding protein, which specficially binds OPG and is involved in osteoclast differentiation. A cDNA clone encoding the murine form of the polypeptide was identified from a library prepared from a mouse myelomonocytic cell line 32-D and transfected into COS cells. Transfectants were screened for their ability to bind to an OPG[22-201]-Fc fusion polypeptide (Example 1). The nucleic acid sequence revealed that OPG binding protein is a novel member of the TNF receptor family and is most closely related to AGP-1, a polypeptide previously described in co-owned and co-pending U.S. Ser. No. 08/660,562, filed Jun. 7, 1996. (A polypeptide identical to AGP-1 and designated TRAIL is described in Wiley et al. Immunity 3, 673–682 (1995)). OPG binding protein is predicted to be a type II transmembrane protein having a cytoplamsic domain at the amino terminus, a transmembrane domain, and a carboxy terminal extracellular domain (FIG. 1). The amino terminal cytoplasmic domain spans about residues 1-48, the transmembrane domain spans about residues 49-69 and the extracellular domain spans about residues 70-316 as shown in FIG. 1 (SEQ ID NO:7). The membrane-associated protein specifically binds OPG (FIG. 2). Thus OPG binding protein and OPG share many characteristics of a receptor-ligand pair although it is possible that other naturally-occurring ligands for OPG binding protein exist.

OPG binding protein refers to a polypeptide having an amino acid sequence of mammalian OPG binding protein, or a fragment, analog, or derivative thereof, and having at least the activity of binding OPG. In preferred embodiments, OPG binding protein is of murine or human origin. In another embodiment, OPG binding protein is a soluble protein having, in one form, an isolated extracellular domain separate from cytoplasmic and transmembrane domains. OPG binding protein is involved in osteoclast differentiation and in the rate and extent of bone resorption.

Nucleic Acids

The invention provides for isolated nucleic acids encoding OPG binding proteins. As used herein, the term nucleic acid comprises cDNA, genomic DNA, wholly or partially synthetic DNA or RNA. The nucleic acids of the invention are selected from the group consisting of:

a) the nucleic acids as shown in FIG. 1 (SEQ ID NO:6);
b) nucleic acids which hybridize to the polypeptide coding regions of the nucleic acids shown in FIG. 1 (SEQ ID NO:6) and remain hybridized to the nucleic acids under high stringency conditions; and
c) nucleic acids which are degenerate to the nucleic acids of (a) or (b).

Nucleic acid hybridizations typically involve a multi-step process comprising a first hybridization step to form nucleic acid duplexes from single strands followed by a second hybridization step carried out under more stringent conditions to selectively retain nucleic acid duplexes having the desired homology. The conditions of the first hybridization step are generally not crucial, provided they are not of higher stringency than the second hybridization step. Generally, the second hybridization is carried out under conditions of high stringency, wherein "high stringency" conditions refers to conditions of temperature and salt which are about 12°–20° C. below the melting temperature ($T_m$) of a perfect hybrid of part or all of the complementary strands corresponding to FIG. 1 (SEQ. ID. NO:7). In one embodiment, "high stringency" conditions refer to conditions of about 65° C. and not more than about 1M Na+. It is understood that salt concentration, temperature and/or length of incubation may be varied in either the first or second hybridization steps such that one obtains the hybridizing nucleic acid molecules according to the invention. Conditions for hybridization of nucleic acids and calculations of $T_m$ for nucleic acid hybrids are described in Sambrook et al. *Molecular Cloning: A Laboratory Manual* Cold Spring Harbor Laboratory Press, New York (1989).

The nucleic acids of the invention may hybridize to part or all of the polypeptide coding regions of OPG binding protein as shown in FIG. 1 (SEQ ID NO:6) and therefore may be truncations or extensions of the nucleic shown therein. Truncated or extended nucleic acids are encompassed by the invention provided that they retain at least the property of binding OPG. In one embodiment, the nucleic acid will encode a polypeptide of at least about 10 amino acids. In another embodiment, the nucleic acid will encode a polypeptide of at least about 20 amino acids. In yet another embodiment, the nucleic acid will encode a polypeptide of at least about 50 amino acids. The hybridizing nucleic acids may also include noncoding sequences located 5' and/or 3' to the OPG binding protein coding regions. Noncoding sequences include regulatory regions involved in expression of OPG binding protein, such as promoters, enhancer regions, translational initiation sites, transcription termination sites and the like.

In preferred embodiments, the nucleic acids of the invention encode mouse or human OPG binding protein. Nucleic acids may encode a membrane bound form of OPG binding protein or soluble forms which lack a functional transmembrane region. The predicted transmembrane region for murine OPG binding protein includes amino acid residues 49-69 inclusive as shown in FIG. 1 (SEQ. ID. NO:7). Substitutions which replace hydrophobic amino acid residues in this region with neutral or hydrophilic amino acid residues would be expected to disrupt membrane association and result in soluble OPG binding protein. In addition, deletions of part or all the transmembrane region would also be expected to produce soluble forms of OPG binding protein. Nucleic acids encoding amino acid residues 70-316 as shown in FIG. 1 (SEQ ID NO:7), or fragments and analogs thereof, encompass soluble OPG binding protein.

Nucleic acid sequences of the invention may be used for the detection of sequences encoding OPG binding protein in biological samples. In particular, the sequences may be used to screen cDNA and genomic libraries for related OPG binding protein sequences, especially those from other species. The nucleic acids are also useful for modulating levels of OPG binding protein by anti-sense technology or in vivo gene expression. Development of transgenic animals expressing OPG binding protein is useful for production of the polypeptide and for the study of in vivo biological activity.

Vectors and Host Cells

The nucleic acids of the invention will be linked with DNA sequences so as to express biologically active OPG binding protein. Sequences required for expression are known to those skilled in the art and include promoters and enhancer sequences for initiation of RNA synthesis, transcription termination sites, ribosome binding sites for the initiation of protein synthesis, and leader sequences for secretion. Sequences directing expression and secretion of OPG binding protein may be homologous, i.e., the sequences are identical or similar to those sequences in the genome involved in OPG binding protein expression and secretion, or they may be heterologous. A variety of plasmid vectors are available for expressing OPG binding protein in host cells (see, for example, Methods in Enzymology v. 185, Goeddel, D. V. ed., Academic Press (1990)). For expression in mammalian host cells, a preferred embodiment is plasmid pDSRα described in PCT Application No. 90/14363. For expression in bacterial host cells, preferred embodiments include plasmids harboring the lux promoter (see co-owned and co-pending U.S. Ser. No. 08/577,778, filed Dec. 22, 1995). In addition, vectors are available for the tissue-specific expression of OPG binding protein in transgenic animals. Retroviral and adenovirus-based gene transfer vectors may also be used for the expression of OPG binding protein in human cells for in vivo therapy (see PCT Application No. 86/00922).

Procaryotic and eucaryotic host cells expressing OPG binding protein are also provided by the invention. Host cells include bacterial, yeast, plant, insect or mammalian cells. OPG binding protein may also be produced in transgenic animals such as mice or goats. Plasmids and vectors containing the nucleic acids of the invention are introduced into appropriate host cells using transfection or transformation techniques known to one skilled in the art. Host cells may contain DNA sequences encoding OPG binding protein as shown in FIG. 1 or a portion thereof, such as the extracellular domain or the cytoplasmic domain. Nucleic acids encoding OPG binding proteins may be modified by substitution of codons which allow for optimal expression in a given host. At least some of the codons may be so-called preference codons which do not alter the amino acid sequence and are frequently found in genes that are highly expressed. However, it is understood that codon alterations to optimize expression are not restricted to the introduction of preference codons. Examples of preferred mammalian host cells for OPG binding protein expression include, but are not limited to COS, CHOd-, 293 and 3T3 cells. A preferred bacterial host cell is *Escherichia coli*.

Polypeptides

The invention also provides OPG binding protein as the product of procaryotic or eucaryotic expression of an exogenous DNA sequence, i.e., OPG binding protein is recombinant OPG binding protein. Exogenous DNA sequences include cDNA, genomic DNA and synthetic DNA sequences. OPG binding protein may be the product of bacterial, yeast, plant, insect or mammalian cells expression, or from cell-free translation systems. OPG binding protein produced in bacterial cells will have an N-terminal methionine residue. The invention also provides for a process of producing OPG binding protein comprising growing procaryotic or eucaryotic host cells transformed or transfected with nucleic acids encoding OPG binding protein and isolating polypeptide expression products of the nucleic acids.

Polypeptides which are mamalian OPG binding protein or are fragments, analogs or derivatives thereof are encompassed by the invention. A fragment of OPG binding protein refers to a polypeptide having a deletion of one or more amino acids such that the resulting polypeptide has at least the property of binding OPG. Said fragments will have deletions originating from the amino terminal end, the carboxy terminal end, and internal regions of the polypeptide. Fragments of OPG binding protein are at least about ten amino acids, at least about 20 amino acids, or at least about 50 amino acids in length. In preferred embodiments, OPG binding protein will have a deletion of one or more amino acids from the transmembrane region (amino acid residues 49-69 as shown in FIG. 1), or, alternatively, one or more amino acids from the amino-terminus up to and/or including the transmembrane region (amino acid residues 1-49 as shown in FIG. 1). In another embodiment, OPG binding protein is a soluble protein comprising, for example, amino acid residues 70-316, or N-terminal or C-terminal truncated forms thereof, which retain OPG binding activity. An analog of an OPG binding protein refers to a polypeptide having a substitution or addition of one or more amino acids such that the resulting polypeptide has at least the property of binding OPG. Said analogs will have substitutions or additions at any place along the polypeptide. Preferred analogs include those of soluble OPG binding proteins. Fragments or analogs may be naturally occurring, such as a polypeptide product of an allelic variant or a mRNA splice variant, or they may be constructed using techniques available to one skilled in the art for manipulating and synthesizing nucleic acids. The polypeptides may or may not have an amino terminal methionine residue Also included in the invention are derivatives of OPG binding protein which are polypeptides that have undergone post-translational modifications (e.g., addition of N-linked or O-linked carbohydrate chains, processing of N-terminal or C-terminal ends), attachment of chemical moieties to the amino acid backbone, chemical modifications of N-linked or O-linked carbohydrate chains, and addition of an N-terminal methionine residue as a result of procaryotic host cell expression. In particular, chemically modified derivatives of OPG binding protein which provide additional advantages such as increased stability, longer circulating time, or decreased immunogenicity are contemplated. Of particular use is modification with water soluble polymers, such as polyethylene glycol and derivatives thereof (see for example U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties. Polypeptides may also be modified at pre-determined positions in the polypeptide, such as at the amino terminus, or at a selected lysine or arginine residue within the polypeptide. Other chemical modificaitons provided include a detectable label, such as an enzymatic, fluorescent, isotopic or affinity label to allow for detection and isolation of the protein.

OPG binding protein chimeras comprising part or all of an OPG binding protein amino acid sequence fused to a heterologous amino acid sequence are also included. The heterologous sequence may be any sequence which allows the resulting fusion protein to retain the at least the activity of binding OPG. In a preferred embodiment, the carboxy terminal extracellular domain of OPG binding protein is fused to a heterologous sequence. Such sequences include heterologous cytoplasmic domains that allow for alternative intracellular signalling events, sequences which promote oligomerization such as the Fc region of IgG, enzyme sequences which provide a label for the polypeptide, and sequences which provide affinity probes, such as an antigen-antibody recognition.

The polypeptides of the invention are isolated and purified from tissues and cell lines which express OPG binding protein, either extracted from lysates or from conditioned growth medium, and from transformed host cells expressing OPG binding protein. OPG binding protein may be obtained from murine myelomonocytic cell line 32-D (ATCC accession no. CRL-11346). Human OPG binding protein, or nucleic acids encoding same, may be isolated from human lymph node or fetal liver tissue. Isolated OPG binding protein is free from association with human proteins and other cell constituents.

A method for the purification of OPG binding protein from natural sources (e.g. tissues and cell lines which normally express OPG binding protein) and from transfected host cells is also encompassed by the invention. The purification process may employ one or more standard protein purification steps in an appropriate order to obtain purified protein. The chromatography steps can include ion exchange, gel filtration, hydrophobic interaction, reverse phase, chromatofocusing, affinity chromatography employing an anti-OPG binding protein antibody or biotin-streptavidin affinity complex and the like.

Antibodies

Antibodies specifically binding the polypeptides of the invention are also encompassed by the invention. The antibodies may be produced by immunization with full-length OPG binding protein, soluble forms of OPG binding protein, or a fragment thereof. The antibodies of the invention may be polyclonal or monoclonal, or may be recombinant antibodies, such as chimeric antibodies wherein the murine constant regions on light and heavy chains are replaced by human sequences, or CDR-grafted antibodies wherein only the complementary determining regions are of murine origin. Antibodies of the invention may also be human antibodies prepared, for example, by immunization of transgenic animals capable of producing human antibodies (see, for example, PCT Application No. WO93/12227). The antibodies are useful for detecting OPG binding protein in biological samples, thereby allowing the identification of cells or tissues which produce the protein In addition, antibodies which bind to OPG binding protein and block interaction with other binding compounds may have therapeutic use in modulating osteoclast differentiation and bone resorption.

Compositions

The invention also provides for pharmaceutical compositions comprising a therapeutically effective amount of the OPG binding protein of the invention together with a pharmaceutically acceptable diluent, carrier, solubilizer, emulsifier, preservative and/or adjuvant. The invention also provides for pharmaceutical compositions comprising a therapeutically effective amount of an OPG binding protein agonist or antagonist. The term "therapeutically effective amount" means an amount which provides a therapeutic effect for a specified condition and route of administration. The composition may be in a liquid or lyophilized form and comprises a diluent (Tris, acetate or phosphate buffers) having various pH values and ionic strengths, solubilizer such as Tween or Polysorbate, carriers such as human serum albumin or gelatin, preservatives such as thimerosal or benzyl alcohol, and antioxidants such as ascrobic acid or sodium metabisulfite. Selection of a particular composition will depend upon a number of factors, including the condition being treated, the route of administration and the pharmacokinetic parameters desired. A more extensive survey of component suitable for pharmaceutical compositions is found in *Remington's Pharmaceutical Sciences*, 18th ed. A. R. Gennaro, ed. Mack, Easton, Pa. (1980).

In a preferred embodiment, compositions comprising soluble OPG binding proteins are also provided. Also encompassed are compositions comprising soluble OPG binding protein modified with water soluble polymers to increase solubility, stability, plasma half-life and bioavailability. Compositions may also comprise incorporation of soluble OPG binding protein into liposomes, microemulsions, micelles or vesicles for controlled delivery over an extended period of time. Soluble OPG binding protein may be formulated into microparticles suitable for pulmonary administration.

Compositions of the invention may be administered by injection, either subcutaneous, intravenous or intramuscular, or by oral, nasal, pulmonary or rectal administration. The route of administration eventually chosen will depend upon a number of factors and may be ascertained by one skilled in the art.

The invention also provides for pharmaceutical compositions comprising a therapeutically effective amount of the nucleic acids of the invention together with a pharmaceutically acceptable adjuvant. Nucleic acid compositions will be suitable for the delivery of part or all of the coding region of OPG binding protein and/or flanking regions to cells and tissues as part of an anti-sense therapy regimen.

Methods of Use

OPG binding proteins may be used in a variety of assays for detecting OPG and characterizing interactions with OPG. In general, the assay comprises incubating OPG binding protein with a biological sample containing OPG under conditions which permit binding to OPG to OPG binding protein, and measuring the extent of binding. OPG may be purified or present in mixtures, such as in body fluids or culture medium. Assays may be developed which are qualitative or quantitative, with the latter being useful for determining the binding parameters (affinity constants and kinetics) of OPG to OPG binding protein and for quantitating levels of biologically active OPG in mixtures. Assays may also be used to evaluate the binding of OPG to fragments, analogs and derivatives of OPG binding protein and to identify new OPG and OPG binding protein family members.

Binding of OPG to OPG binding protein may be carried out in several formats, including cell-based binding assays, membrane binding assays, solution-phase assays and immunoassays. In general, trace levels of labeled OPG are incubated with OPG binding protein samples for a specified period of time followed by measurement of bound OPG by filtration, electrochemiluminescent (ECL, ORIGEN system by IGEN), cell-based or immunoassays. Homogeneous assay technologies for radioactivity (SPA; Amersham) and time resolved fluoresence (HTRF, Packard) can also be implemented. Binding is detected by labeling OPG or an anti-OPG antibody with radioactive isotopes (125I, 35S, 3H), fluorescent dyes (fluorescein), lanthanide (Eu3+) chelates or cryptates, orbipyridyl-ruthenium (Ru2+) complexes. It is understood that the choice of a labeled probe will depend upon the detection system used. Alternatively, OPG may be modified with an unlabled epitope tag (e.g., biotin, peptides, $His_6$, myc) and bound to proteins such as streptavidin, anti-peptide or anti-protein antibodies which have a detectable label as described above.

In an alternative method, OPG binding protein may be assayed directly using polyclonal or monoclonal antibodies to OPG binding proteins in an immunoassay. Additional forms of OPG binding proteins containing epitope tags as described above may be used in solution and immunoassays.

Methods for indentifying compounds which interact with OPG binding protein are also encompassed by the invention. The method comprises incubating OPG binding protein with a compound under conditions which permit binding of the compound to OPG binding protein, and measuring the extent of binding. The compound may be substantially purified or present in a crude mixture. Binding compounds may be nucleic acids, proteins, peptides, carbohydrates, lipids or small molecular weight organic compounds. The compounds may be further characterized by their ability to increase or decrease OPG binding protein activity in order to determine whether they act as an agonist or an antagonist.

OPG binding proteins are also useful for identification of intracellular proteins which interact with the cytoplasmic domain by a yeast two-hybrid screening process. As an example, hybrid constructs comprising DNA encoding the N-terminal 50 amino acids of an OPG binding protein fused to a yeast GAL4-DNA binding domain may be used as a two-hybrid bait plasmid. Positive clones emerging from the screening may be characterized further to identify interacting proteins. This information may help elucidate a intracellular signaling mechanism associated with OPG binding protein and provide intracellular targets for new drugs that modulate bone resorption.

The invention also encompasses modulators (agonists and antagonists) of OPG binding protein and the methods for obtaining them. An OPG binding protein modulator may either increase or decrease at least one activity associated with OPG binding protein, such as ability to bind OPG or some other interacting molecule or to regulate osteoclast maturation. Typically, an agonist or antagonist may be a co-factor, such as a protein, peptide, carbohydrate, lipid or small molecular weight molecule, which interacts with OPG binding protein to regulate its activity. Potential polypeptide antagonists include antibodies which react with either soluble or membrane-associated forms of OPG binding protein, and soluble forms of OPG binding protein which comprise part or all of the extracellular domain of OPG binding protein. Molecules which regulate OPG binding protein expression typically include nucleic acids which are complementary to nucleic acids encoding OPG binding protein and which act as anti-sense regulators of expression.

OPG binding protein is involved in controlling formation of mature osteoclasts, the primary cell type implicated in bone resorption. An increase in the rate of bone resorption (over that of bone formation) can lead to various bone disorders collectively referred to as osteopenias, and include osteoporosis, osteomyelitis, hypercalcemia, osteopenia brought on by surgery or steroid administration, Paget's disease, osteonecrosis, bone loss due to rheumatoid arthritis, periodontal bone loss, and osteolytic metastasis. Conversely, a decrease in the rate of bone resportion can lead to osteopetrosis, a condition marked by excessive bone density. Agonists and antagonists of OPG binding protein modulate osteoclast formation and may be administered to patients suffering from bone disorders. Agonists and antagonists of OPG binding protein used for the treatment of osteopenias may be administered alone or in combination with a therapeutically effective amount of a bone growth promoting agent including bone morphogenic factors designated BMP-1 to BMP-12, transforming growth factor-β and TGF-β family members, interleukin-1 inhibitors, TNFα inhibitors, parathyroid hormone, E series prostaglandins, bisphosphonates and bone-enhancing minerals such as fluoride and calcium.

The following examples are offered to more fully illustrate the invention, but are not construed as limiting the scope thereof.

EXAMPLE 1

Identification of a Cell Line Source for an OPG Binding Protein

Osteoprotegerin (OPG) negatively regulates osteoclastogenesis in vitro and in vivo. Since OPG is a TNFR-related protein, it is likely to interact with a TNF-related family member while mediating its effects. With one exception, all known members of the TNF superfamily are type II transmembrane proteins expressed on the cell surface. To identify a source of an OPG binding protein, recombinant OPG-Fc fusion proteins were used as immunoprobes to screen for OPG binding proteins located on the surface of various cell lines and primary hematopoietic cells.

Cell lines that grew as adherent cultures in vitro were treated using the following methods: Cells were plated into 24 well tissue culture plates (Falcon), then allowed to grow to approxiamtely 80% confluency. The growth media was then removed, and the adherent cultures were washed with phosphate buffered saline (PBS) (Gibco) containing 1% fetal calf serum (FCS). Recombinant mouse OPG [22-194]-Fc and human OPG [22-201]-Fc fusion proteins (see U.S. Ser. No. 08/706,945 filed Sep. 3, 1996) were individually diluted to 5 ug/ml in PBS containing 1% FCS, then added to the cultures and allowed to incubate for 45 min at 0° C. The OPG-Fc fusion protein solution was discarded, and the cells were washed in PBS-FCS solution as described above. The cultures were then exposed to phycoeyrthrin-conguated goat F(ab') anti-human IgG secondary antibody (Southern Biotechnology Associates Cat. #2043-09) diluted into PBS-FCS. After a 30–45 min incubation at 0° C., the solution was discarded, and the cultures were washed as described above. The cells were then analysed by immunofluorescent microscopy to detect cell lines which express a cell surface OPG binding protein.

Suspension cell cultures were analysed in a similar manner with the following modifications: The diluent and wash buffer consisted of calcium- and magnesium-free phosphate buffered saline containing 1% FCS. Cells were harvested from exponentially replicating cultures in growth media, pelleted by centrifugation, then resuspended at 1×10⁷ cells/ml in a 96 well microtiter tissue culture plate (Falcon). Cells were sequentially exposed to recombinant OPG-Fc fusion proteins, then secondary antibody as described above, and the cells were washed by centrifugation between each step. The cells were then analysed by fluorescence activated cell sorting (FACS) using a Becton Dickinson FACscan.

Using this approach, the murine myelomonocytic cell line 32D (ATCC accession no. CRL-11346) was found to express a surface molecule which could be detected with both the mouse OPG[22-194]-Fc and the human OPG[22-201]-Fc fusion proteins. Secondary antibody alone did not bind to the surface of 32D cells nor did purified human IgG1 Fc, indicating that binding of the OPG-Fc fusion proteins was due to the OPG moiety. This binding could be competed in a dose dependent manner by the addition of recombinant murine or human OPG[22-401] protein. Thus the OPG region required for its biological activity is capable of specifically binding to a 32D-derived surface molecule.

EXAMPLE 2

Expression Cloning of a Murine OPG Binding Protein

A cDNA library was prepared from 32D mRNA, and ligated into the mammalian expression vector pcDNA3.1(+)

(Invitrogen, San Diego, Calif.). Exponentially growing 32D cells maintained in the presence of recombinant interleukin-3 were harvested, and total cell RNA was purified by acid guanidinium thiocyanate-phenol-chloroform extraction (Chomczynski and Sacchi. Anal. Biochem. 162, 156–159, (1987)). The poly (A+) mRNA fraction was obtained from the total RNA preparation by adsorption to, and elution from, Dynabeads Oligo (dT)25 (Dynal Corp) using the manufacturer's recommended procedures. A directional, oligo-dT primed cDNA library was prepared using the Superscript Plasmid System (Gibco BRL, Gaithersburg, Md.) using the manufacturer's recommended procedures. The resulting cDNA was digested to completion with Sal I and Not I restriction endonuclease, then fractionated by size exclusion gel chromatography. The highest molecular weight fractions were selected, and then ligated into the polyliker region of the plasmid vector pcDNA3.1(+) (Invitrogen, San Diego, Calif.). This vector contains the CMV promotor upstream of multiple cloning site, and directs high level expression in eukaryotic cells. The library was then electroporated into competent $E.$ $coli$ (ElectroMAX DH10B, Gibco, N.Y.), and titered on LB agar containing 100 ug/ml ampicillin. The library was then arrayed into segregated pools containing approximately 1000 clones/pool, and 1.0 ml cultures of each pool were grown for 16–20 hr at 37° C. Plasmid DNA from each culture was prepared using the Qiagen Qiawell 96 Ultra Plasmid Kit (catalog #16191) following manufacturer's recommended procedures.

Arrayed pools of 32D cDNA expression library were individually lipofected into COS-7 cultures, then assayed for the acquisition of a cell surface OPG binding protein. To do this, COS-7 cells were plated at a density of $1 \times 10^6$ per ml in six-well tissue culture plates (Costar), then cultured overnight in DMEM (Gibco) containing 10% FCS. Approximately 2 $\mu$g of plasmid DNA from each pool was diluted into 0.5 ml of serum-free DMEM, then sterilized by centrifugation through a 0.2 $\mu$m Spin-X column (Costar). Simultaneously, 10 $\mu$l of Lipofectamine (Life Technologies Cat #18324-012) was added to a separate tube containing 0.5 ml of serum-free DMEM. The DNA and Lipofectamine solutions were mixed, and allowed to incubate at RT for 30 min. The COS-7 cell cultures were then washed with serum-free DMEM, and the DNA-lipofectamine complexes were exposed to the cultures for 2–5 hr at 37° C. After this period, the media was removed, and replaced with DMEM containing 10% FCS. The cells were then cultured for 48 hr at 37° C.

To detect cultures that express an OPG binding protein, the growth media was removed, and the cells were washed with PBS-FCS solution. A 1.0 ml volume of PBS-FCS containing 5 $\mu$ml of human OPG[22-201]-Fc fusion protein was added to each well and incubated at RT for 1 hr. The cells were washed three times with PBS-FCS solution, and then fixed in PBS containing 2% paraformaldehyde and 0.2% glutaraldehyde in PBS at RT for 5 min. The cultures were washed once with PBS-FCS, then incubated for 1 hr at 65° C. while immersed in PBS-FCS solution. The cultures were allowed to cool, and the PBS-FCS solution was aspirated. The cultures were then incubated with an alkaline-phosphatase conjugated goat anti-human IgG (Fc specific) antibody (SIGMA Product #A-9544) at Rt for 30 min, then washed three-times with 20 mM Tris-Cl (pH 7.6), and 137 mM NaCl. Immune complexes that formed during these steps were detected by assaying for alkaline phosphatase activity using the Fast Red TR/AS-MX Substrate Kit (Pierce, Cat. #34034) following the manufacturer's recommended procedures.

Using this approach, a total of approximately 300,000 independent 32D cDNA clones were screened, represented by 300 transfected pools of 1000 clones each. A single well was identifed that contained cells which acquired the ability to be specifically decorated by the OPG-Fc fusion protein. This pool was subdivided by sequential rounds of sib selection, yeilding a single plasmid clone 32D-F3 (FIG. 1). 32D-F3 plasmid DNA was then transfected into COS-7 cells, which were immunostained with either FITC-conjugated goat anti-human IgG secondary antibody alone, human OPG[22-201]-Fc fusion protein plus secondary, or with ATAR-Fc fusion protein (ATAR also known as HVEM; Montgomery et al. Cell 87, 427–436 (1996)) (FIG. 2). The secondary antibody alone did not bind to COS-7/32D-F3 cells, nor did the ATAR-Fc fusion protein. Only the OPG Fc fusion protein bound to the COS-7/32D-F3 cells, indicating that 32D-F3 encoded an OPG binding protein displayed on the surface of expressing cells.

EXAMPLE 3

OPG Binding Protein Sequence

The 32D-F3 clone isolated above contained an approximately 2.3 kb cDNA insert (FIG. 1), which was sequenced in both directions on an Applied Biosystems 373A automated DNA sequencer using primer-driven Taq dye-terminator reactions (Applied Biosystems) following the manufacturer's recommended procedures. The resulting nucleotide sequence obtained was compared to the DNA sequence database using the FASTA program (GCG, Univeristy of Wisconsin), and analysed for the presence of long open reading frames (LORF's) using the "Six-way open reading frame" application (Frames) (GCG, Univeristy of Wisconsin). A LORF of 316 amino acid (aa) residues beginning at methionine was detected in the appropriate orientation, and was preceded by a 5' untranslated region of about 150 bp. The 5' untranslated region contained an in-frame stop codon upstream of the predicted start codon. This indicates that the structure of the 32D-F3 plasmid is consistent with its ability to utilize the CMV promotor region to direct expression of a 316 aa gene product in mammalian cells.

The predicted OPG binding protein sequence was then compared to the existing database of known protein sequences using a modified version of the FASTA program (Pearson, Meth. Enzymol. 183, 63–98 (1990)). The amino acid sequence was also analysed for the presence of specific motifs conserved in all known members of the tumor necrosis factor (TNF) superfamily using the sequence profile method of (Gribskov et al. Proc. Natl. Acad. Sci. USA 83, 4355–4359 (1987)), as modified by Luethy et al. Protein Sci. 3, 139–146 (1994)). There appeared to be significant homology throughout the OPG binding protein to several members of the TNF superfamily. The mouse OPG binding protein appear to be most closely related to the mouse and human homologs of both TRAIL and CD40. Further analysis of the OPG binding protein sequence indicated a strong match to the TNF superfamily, with a highly significant Z score of 19.46.

The OPG binding protein aa sequence contains a probable hydrophobic transmembrane domain that begins at a M49 and extends to L69. Based on this configuration relative to the methionine start codon, the OPG binding protein is predicted to be a type II transmembrane protein, with a short N-terminal intracellular domain, and a longer C-terminal extracellular domain (FIG. 4). This would be similar to all known TNF family members, with the exception of lymphotoxin alpha (Nagata and Golstein, Science 267, 1449–1456 (1995)).

EXAMPLE 4

Expression of Human OPG Binding Protein mRNA

Multiple human tissue northern blots (Clontech, Palo Alto, Calif.) were probed with a $^{32}$P-dCTP labelled 32D-F3 restriction fragment to detect the size of the human transcript and to determine patterns of expression. Northern blots were prehybridized in 5X SSPFE, 50% formamide, 5X Denhardt's solution, 0.5% SDS, and 100 μ/ml denatured salmon sperm DNA for 2–4 hr at 42° C. The blots were then hybridized in 5X SSPE, 50% formamide, 2X Denhardt's solution, 0.1% SDS, 100 μ/ml denatured salmon sperm DNA, and 5 ng/ml labelled probe for 18–24 hr at 42° C. The blots were then washed in 2X SSC for 10 min at RT, 1X SSC for 10 min at 50° C., then in 0.5X SSC for 10–15 min.

Figure 3:
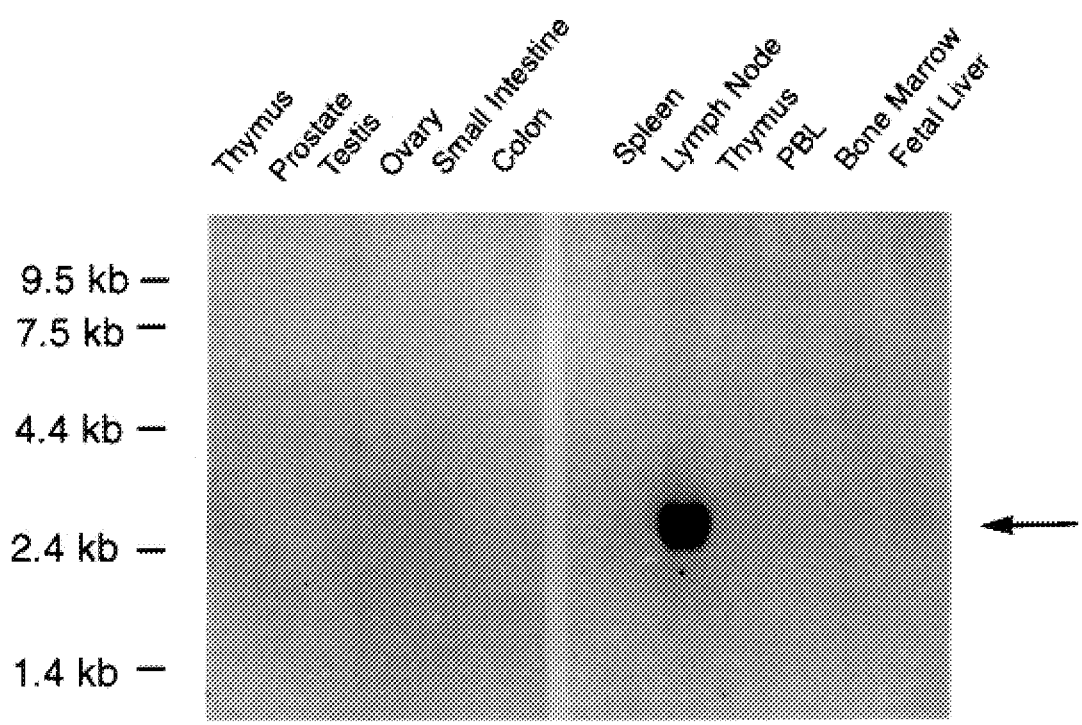
FIG. 3. Expression of OPG binding protein in human tissues. Northern blot analysis of human tissue mRNA (Clontech) using a radiolabeled 32D-F3 derived hybridization probe. Relative molecular mass is indicated at the left in kilobase pairs (kb). Arrowhead on right side indicates the migration of an approximately 2.5 kb transcript detected in lymph node mRNA. A very faint band of the same mass is also detected in fetal liver.

Using a probe derived from the mouse cDNA and hybridization under stringent conditions, a predominant mRNA species with a relative molecular mass of about 2.5 kb was detected in lymph nodes (FIG. 3). A faint signal was also detected at the same relative molecular mass in fetal liver mRNA. No OPG binding protein transcripts were detected in the other tissues examined. The data suggest that expression of OPG binding protein mRNA was extremely restricted in human tissues. The data also indicate that the cDNA clone isolated is very close to the size of the native transcript, suggesting 32D-F3 is a full length clone.

EXAMPLE 5

Molecular Cloning of the Human OPG Binding Protein

The human homolog of the OPG binding protein is expressed as an approximately 2.5 kb mRNA in human peripheral lymph nodes and is detected by hybridization with a mouse cDNA probe under stringent hybdization conditions. DNA encoding human OPG binding protein is obtained by screening a human lymph node cDNA library by either recombinant bacteriphage plaque, or transformed bacterial colony, hybridiziation methods (Sambrook et al. *Molecular Cloning: A Laboratory Manual* Cold Spring Harbor Press, New York (1989)). To this the phage or plasmid cDNA library are screened using radioactively-labeled probes derived from the murine OPG binding protein clone 32D-F3. The probes are used to screen nitrocellulose filter lifted from a plated library. These filters are prehybridized and then hybridized using conditions specified in Example 4, ultimately giving rise to purified clones of the human OPG binding protein cDNA. Inserts obtained from any human OPG binding protein clones would be sequenced and analysed as described in Example 3.

EXAMPLE 6

Cloning and Bacterial Expression of OPG Binding Protein

PCR amplification employing the primer pairs and templates described below are used to generate various forms of human OPG binding proteins. One primer of each pair introduces a TAA stop codon and a unique SacII site following the carboxy terminus of the gene. The other primer of each pair introduces a unique NdeI site, a N-terminal methionine, and optimized codons for the amino terminal portion of the gene. PCR and thermocycling is performed using standard recombinant DNA methodology. The PCR products are purified, restriction digested, and inserted into the unique NdeI and SacII sites of vector pAMG21 (ATCC accession no. 98113) and transformed into the prototrophic *E. coli* 393. Other commonly used *E. coli* expression vectors and host cells are also suitable for expression. After transformation, the clones are selected, plasmid DNA is isolated and the sequence of the OPG binding protein insert is confirmed.

pAMG21-Murine OPG Binding Protein [75-316]

This construct is engineered to be 242 amino acids in length and have the following N-terminal and C-terminal residues, $NH_2$-Met (75)-Asp-Pro-Asn-Arg - - - Gln-Asp-Ile-Asp(316)-COOH. The template to be used for PCR is pcDNA/32D-F3 and oligonucleotides #1581-72 and #1581-76 will be the primer pair to be used for PCR and cloning this gene construct.

1581-72:

5'-GTTCTCCTCATATGGATCCAAACCGTATTTCTGAAGACAGCACTCACTGCTT-3'
(SEQ ID NO: 1)

1581-76:

5'-TACGCACTCCGCGGTTAGTCTATGTCCTGAACTTTGA-3'
(SEQ ID NO: 2)

pAMG21-Murine OPG Binding Protein [158-316]

This construct is engineered to be 160 amino acids in length and have the following N-terminal and C-terminal residues, $NH_2$-Met-Lys (158)-Pro-Glu-Ala - - - Gln-Asp-Ile-Asp(316)-COOH. The template to be used for PCR is pcDNA/32D-F3 and oligonucleotides #1581-73 and #1581-76 will be the primer pair to be used for PCR and cloning this gene construct.

1581-73:

5'-GTTCTCCTCATATGAAACCTGAAGCTCAACCATTTGCACACCTCACCATCAAT-3'
(SEQ ID NO: 3)

1581-76:

5'-TACGCACTCCGCGGTTAGTCTATGTCCTGAACTTTGA-3'
(SEQ ID NO: 2)

pAMG21-Murine OPG Binding Protein [166-316]

This construct is engineered to be 152 amino acids in length and have the following N-terminal and C-terminal residues, $NH_2$-Met-His(166)-Leu-Thr-Ile - - - Gln-Asp-Ile-Asp(316)-COOH. The template to be used for PCR is pcDNA/32D-F3 and oligonucleotides #1581-75 and #1581-76 will be the primer pair to be used for PCR and cloning this gene construct.

1581-75:

5'-GTTCTCCTCATATGCATTTAACTATTAACGCTGCATCTATCCCATCGGGTTCCCATAAAGTCACT-3'
(SEQ ID NO: 4)

1581-76:

5'-TACGCACTCCGCGGTTAGTCTATGTCCTGAACTTTGA-3'
(SEQ ID NO: 2)

pAMG21-Murine OPG Binding Protein [168-316]

This construct is engineered to be 150 amino acids in length and have the following N-terminal and C-terminal residues, $NH_2$-Met-Thr(168)-Ile-Asn-Ala - - - Gln-Asp-Ile-Asp(316)-COOH. The template to be used for PCR is pcDNA/32D-F3 and oligonucleotides #1581-74 and #1581-76 will be the primer pair to be used for PCR and cloning.

1581-74:

5'-GTTCTCCTCATATGACTATTAACGCTGCATCTATCCCATCGGGTTCCCATAAAGTCACT-3'
(SEQ ID NO: 5)

1581-76:

5'-TACGCACTCCGCGGTTAGTCTATGTCCTGAACTTTGA-3'
(SEQ ID NO: 2)

It is understood that the above constructs are examples and one skilled in the art may readily obtain other forms of OPG binding protein using the general methodology presented her.

Growth of transfected *E. coli* 393, induction of OPG binding protein expression and isolation of inclusion bodies containing OPG binding protein is done according to procedures described in U.S. Ser. No. 08/577,788 filed Dec. 22, 1995. Subsequent purification of OPG binding proteins expressed in *E. coli* requires solubilization of bacteria inclusion bodies and renaturing of OPG binding protein using procedures available to one skilled in the art.

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. A purified and isolated osteoprotegerin binding protein.

2. The protein of claim 1 which is a human osteoprotegerin binding protein.

3. The protein of claim 1 having the amino acid sequence as shown in FIG. 1 (SEQ ID NO:7).

4. The protein of claim 1 which has been covalently modified with a water-soluble polymer.

5. The protein of claim 4 wherein the polymer is polyethylene glycol.

6. The protein of claim 1 which is a soluble osteoprotegerin binding protein.

7. The protein of claim 6 having the amino acid sequence from residues 70-316 inclusive as shown in FIG. 1 (SEQ ID NO:7).

8. A fragment, analog, or derivative of the soluble osteoprotegerin binding protein of claim 7, said fragment, analog, or derivative having the ability to bind osteoprotegerin.

9. A fragment, analog, or derivative of the osteoprotegerin binding protein of claim 1, said fragment, analog, or derivative having the ability to bind osteoprotegerin.

10. The protein of claim 1 which is fused to a heterologous protein sequence and retains osteoprotegerin binding activity.

11. A purified and isolated polypeptide encoded by the nucleic acid sequence shown in FIG. 1 (SEQ ID NO:6) or a nucleic acid sequence which hybridizes under the high stringency conditions of 65° C. and 1M Na$^+$ to the nucleic acid sequence shown in FIG. 1 (SEQ ID NO:6), said polypeptide having the ability to bind osteoprotegerin.

12. A purified and isolated polypeptide having the ability to bind osteoprotegerin, said polypeptide produced by a process comprising growing under suitable nutrient conditions host cells transformed or transfected with the sequence shown in FIG. 1 (SEQ ID NO:6) or a nucleic acid sequence which hybridizes under the high stringency conditions of 65° C. and 1M Na$^+$ to the nucleic acid sequence shown in FIG. 1 (SEQ ID NO:6), and isolating the polypeptide product resulting from the expression of the nucleic acid, said polypeptide having the ability to bind osteoprotegerin.

13. A pharmaceutical composition comprising a therapeutically effective amount of an osteoprotegerin binding protein in a pharmaceutically acceptable carrier, adjuvant, solubilizer, stabilizer and/or anti-oxidant.

14. The composition of claim 13 wherein the osteoprotegerin binding protein is a human osteoprotegerin binding protein.

15. A method for detecting the presence of osteoprotegerin in a biological sample comprising:

incubating the sample with an osteoprotegerin binding protein under conditions that allow binding of the protein to osteoprotegerin; and measuring the bound osteoprotegerin binding protein.

* * * * *